United States Patent
Koch et al.

(10) Patent No.: US 10,307,699 B2
(45) Date of Patent: Jun. 4, 2019

(54) FILTERING ELEMENT

(75) Inventors: Edwin Koch, Tholey (DE); Matthias Schwender, Kirkel (DE); Andreas Schmitz, Kirkel (DE)

(73) Assignee: HYDAC FILTERTECHNIK GMBH, Sulzbach/Saar (DE)

( * ) Notice: Subject to any disclaimer, the term of this patent is extended or adjusted under 35 U.S.C. 154(b) by 960 days.

(21) Appl. No.: 13/809,849

(22) PCT Filed: Jul. 8, 2011

(86) PCT No.: PCT/EP2011/003421
§ 371 (c)(1),
(2), (4) Date: Feb. 22, 2013

(87) PCT Pub. No.: WO2012/007135
PCT Pub. Date: Jan. 19, 2012

(65) Prior Publication Data
US 2013/0180899 A1  Jul. 18, 2013

(30) Foreign Application Priority Data
Jul. 14, 2010  (DE) .......... 10 2010 027 038

(51) Int. Cl.
*G01N 21/81* (2006.01)
*B01D 36/00* (2006.01)
(Continued)

(52) U.S. Cl.
CPC .......... *B01D 35/143* (2013.01); *B01D 36/003* (2013.01); *B01D 36/005* (2013.01);
(Continued)

(58) Field of Classification Search
CPC ........ G01N 21/01; G01N 21/77; G01N 21/78; G01N 21/81; G01N 21/85; G01N 21/8803;
(Continued)

(56) References Cited

U.S. PATENT DOCUMENTS 4,033,881 A * 7/1977 Pall .................. B01D 29/54
210/491
4,150,570 A * 4/1979 Fuller .................. 73/335.01
(Continued)

FOREIGN PATENT DOCUMENTS

DE  69 19 836 U  9/1969
DE  691836  *  9/1969  .......... B01D 35/027
(Continued)

OTHER PUBLICATIONS

Jill Kunzelman, Brent R. Crenshaw and Christoph Weder, Self-assembly of chromogenic dyes—a new mechanism for humidity sensors, J. Mater. Chem., 2007,17, 2989-2991 (availible at http://pubs.rsc.org/en/content/articlepdf/2007/jm/b705880b).*
(Continued)

*Primary Examiner* — Heidi R Kelley
*Assistant Examiner* — Angel Olivera
(74) *Attorney, Agent, or Firm* — Slayden Grubert Beard PLLC

(57) ABSTRACT

A filtering element for filtering devices, comprising a filtering material (5) which defines a filtering space and is intended for the filtration of fluids, and at least one water indicator (13, 19, 23) which is provided at a location coming into contact with fluid during the filtration mode and indicates the presence of water in the fluid in a visually recognizable manner, is characterized in that the at least one water indicator (13, 19, 23) is provided on an end cap (7, 9) for mounting at one end of the filtering material (5), and/or is at least partially part of the end cap (7, 9), and/or is provided on a fluid-permeable supporting structure (21) surrounding the filtering material (5), and/or is at least partially part of the supporting structure (21).

14 Claims, 3 Drawing Sheets

(51) Int. Cl.
    B01D 27/10 (2006.01)
    B01D 35/143 (2006.01)

(52) U.S. Cl.
    CPC ............ *G01N 21/81* (2013.01); *B01D 27/101* (2013.01); *B01D 2201/0407* (2013.01); *B01D 2201/0415* (2013.01); *B01D 2201/291* (2013.01); *B01D 2201/52* (2013.01)

(58) Field of Classification Search
    CPC ......... G01N 31/222; G01N 2021/0106; G01N 2021/7759; G01N 2021/7796; B01D 27/00–148; B01D 35/143; B01D 36/005; B01D 2201/0407; B01D 36/003; B01D 27/101; B01D 2201/52; B01D 2201/291; B01D 2201/0415
    See application file for complete search history.

(56) References Cited

U.S. PATENT DOCUMENTS

| | | | | |
|---|---|---|---|---|
| 2005/0193623 A1* | 9/2005 | Freeman | ................ | C10G 33/06 44/639 |
| 2007/0251875 A1* | 11/2007 | Koch | .................... | B01D 29/15 210/243 |

FOREIGN PATENT DOCUMENTS

| | | |
|---|---|---|
| DE | 202005013908 U1 | 2/2007 |
| EP | 1 340 976 A1 | 9/2003 |
| EP | 1 813 491 A2 | 8/2007 |
| EP | 1 844 835 A2 | 10/2007 |
| GB | 345672 A * 3/1931 | ........... G01N 31/222 |

OTHER PUBLICATIONS

Harris, Arlo D., and Lee H. Kalbus. "Decomposition of Copper(II) Sulfate Pentahydrate: A Sequential Gravimetric Analysis". Journal of Chemical Education 56.6 (1979): 417. DOI: 10.1021/ed056p417.*
"Test Strip". 2017. En.Wikipedia.Org. Accessed Jul. 22, 2017. Edited Mar. 21, 2013. https://en.wikipedia.org/wiki/Test_strip.*
"Test Strip Definition and Meaning | Collins English Dictionary". 2017. Collinsdictionary.Com. Accessed Jul. 22, 2017. https://www.collinsdictionary.com/dictionary/english/test-strip.*
European Patent Office, International Search Report with Written Opinion of the International Searching Authority dated Sep. 7, 2011, International Application No. PCT/EP2011/003421.
German Patent Office, Office Action of DE 10 2010 027 038.5-14 dated Mar. 29, 2011.

* cited by examiner

FILTERING ELEMENT

BACKGROUND OF THE INVENTION

The invention relates to a filtering element for filtering devices comprising a filtering material which defines a filtering space, intended for the filtration of fluids, such as hydraulic fluids, and at least one water indicator which is provided at a location coming into contact with a fluid during filtration mode and indicates the presence of water in the fluid in a visually recognizable manner.

For the operational safety of hydraulic systems and other technical installations that work with fluid operating materials, operational safety largely depends on the associated filtering devices working trouble-free. A requisite for this is for the filtering elements of the filtering devices to remain fully and perfectly functional over the entire time of use between the specified filter changes. In view of the high material value of the relevant hydraulic systems and the cost associated with failure, one is forced to pay particular attention to maintaining the specified operating conditions to prevent potential malfunctions. When filtering elements are removed at the exchange intervals, the filtering elements are therefore carefully checked for potential damage which arose during operation. However, it has been shown in practice that, when damage or impairments are identifiable with, for example, the filtering medium of the removed filtering element, it is difficult or even impossible to deduce the precise cause of the impairment or damage.

A filtering element of the initially cited type is known from DE 69 19 836 U. An oil furnace tank filter is known that consists of a cylindrical body open on top with a molded-on base in whose top open part a filling funnel is arranged with at least one contaminant separating filter arranged therein, and a mechanical sludge and water trap is provided in its base. A water indicator is arranged at the top contaminant separating filter and on the base of the cylindrical body. The water indicator can consist of a water-indicating reaction paper, a water-indicating granulate, or a paste. The water-indicating indicators make it possible to remove water that is present in a timely manner from the device.

Today's highly effective filtering media react problematically to the presence of water in fluid so that the filtering effect can suffer from operation with fluids that are contaminated with a proportion of water. If the filtration quality decreases while operating a hydraulic system without exceeding the permissible operating limits such as the pressure level, maximum volumetric flow, differential pressure (bypass valve response) or the like, it can be determined whether the problem was caused by water in the fluid while changing the filtering element. The system operator is therefore able to undertake the appropriate, corresponding countermeasures and thereby cause the trouble-free filtration mode.

In view of these problems, the object of the invention is to provide a filtering element whose use promotes the safe operation of the filtering device and hence the associated system and makes it possible to easily manufacture the filtering element.

SUMMARY

According to the invention, this object is achieved by a filtering element having the features of all of claim 1. Accordingly, an essential characteristic of the invention is that at least one water indicator is provided on at least one end cap for encasement at one end of the filtering material defining a filtering space, especially a filtering cavity, and/or is at least partially part of the end cap, and/or it is provided on a supporting structure for surrounding a filtering material which defines a filtering space, especially a filtering cavity, and/or is at least partially part of the supporting structure. Advantageous embodiments of the filtering element according to the invention are the subject of the dependent claims.

A water indicator that is typically in the form of a test strip or as a receptacle for a corresponding material can be easily fastened to an end cap and/or supporting structure which simplifies the overall production of the filtering element according to the invention. Both components, the end cap and supporting structure, offer external surfaces for attaching or respectively adhering a test strip and/or for being coated with a corresponding substance or respectively material serving as the water indicator. The top end cap is recommendable for forming a typically trough-shaped receptacle for a water indicator or respectively corresponding substance. A plurality of water indicators can be provided on the filtering element, on end caps and/or a supporting structure, which allows the location of the occurrence of water to be identified during filtration mode.

The end cap or supporting structure itself can be designed as the water indicator, for example by consisting of a multicomponent material such as a plastic material, of which one material component serves as a water indicator. Alternatively, the end cap or supporting structure can be provided with a coating containing the water indicator. It is however also conceivable to design only parts of the surface or volume of the end cap or supporting structure as the water indicator, or respectively provide them with a water indicator. A water indicator is usefully adapted to the anticipated operating temperature during the filtration mode, or respectively chosen requirements-oriented. For a filtering element that operates in a large temperature and/or pressure range a plurality of water indicators with different designs can be provided.

If the water indicator is arranged at a location that is visually observable while the filtering element is removed from the filtering device, the operator can identify any contamination of the fluid with water by the immediate appearance without particular measures or tools being necessary.

The arrangement can be advantageously such that the respective water indicator is provided on the outside of the respective end cap. A water indicator can be attached in a particularly easy manner to the end cap in the form of a test strip containing copper sulfate, for example by being adhered. Copper sulfate assumes an intense green-blue color upon contact with water that is visually very easy to identify. Alternately, a receptacle can be formed on the respective end cap for the water indicator marketed under the brand name of "Silicagel" which changes color upon contact.

In addition, when there is a fluid-permeable supporting structure located on the outside of its filtering material, it is possible for the filtering element to have the water indicator on the supporting structure. The arrangement can be advantageously such that the outside of the supporting structure is provided with a marking, especially labeling, that contains substances such as copper sulfate serving as the water indicator.

It can be particularly advantageous when at least one water indicator is provided that signals the presence of water by changing color, wherein a water indicator that irreversibly changes color in the presence of water can preferably be used.

The invention will be explained in detail below with reference to exemplary embodiments shown in the drawings.

DETAILED DESCRIPTION OF PREFERRED EMBODIMENTS

Figure 1:
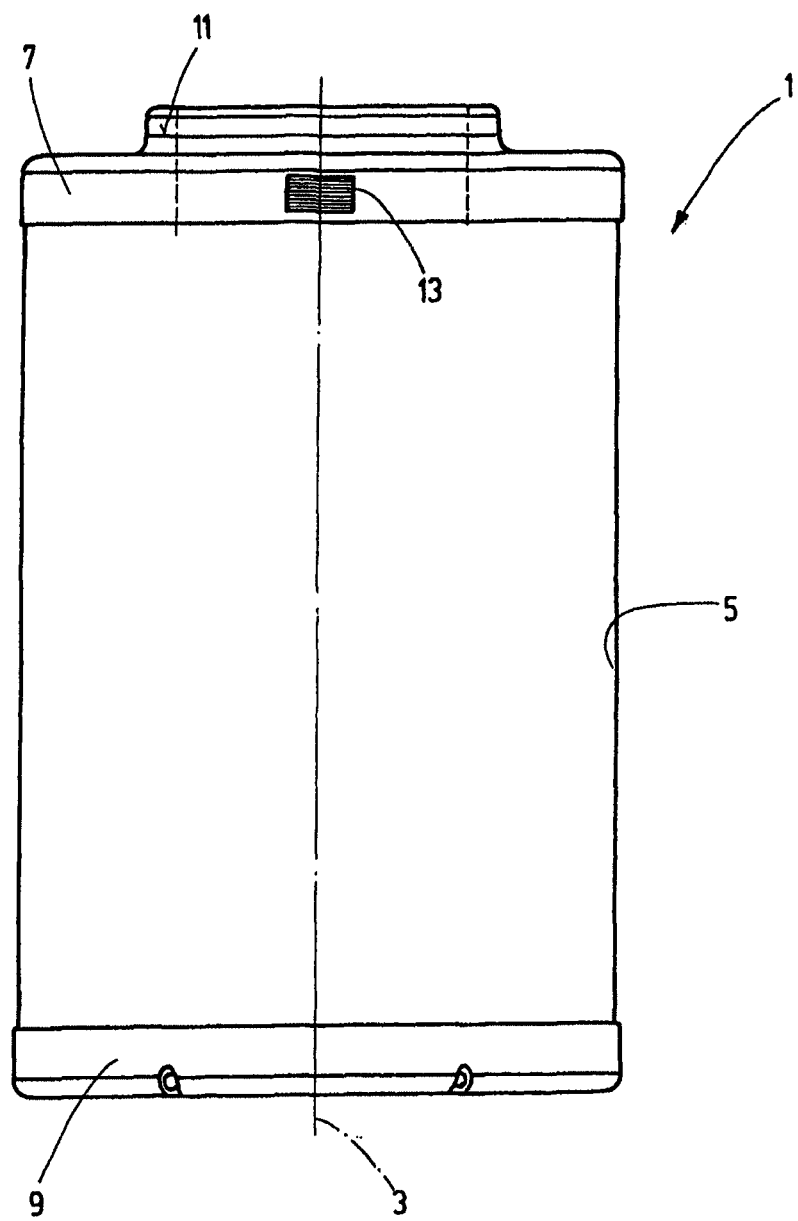
FIG. 1 shows a schematically simplified drawing of a side view of an exemplary embodiment of the filtering element according to the invention.

In the following, the invention will be explained with reference to a filtering element 1 that can be exchangeably accommodated in a filtering housing (not shown) of a filtering device. The filtering element 1 is designed in an overall circular cylindrical way with reference to a longitudinal axis 3 and has a top end cap 7 and a bottom end cap 9 as terminal encasements of a filtering material 5, of which the top end cap 7, for example, forms a fluid passage 11 into an inner filtering cavity within the filtering material 5 in the manner which is usual for such filtering elements.

In the exemplary embodiment in FIG. 1, there is a water indicator in the form of a test strip 13 on the side wall surface of the top end cap 7. This is a paper strip, on which there is copper sulfate, adhered to the end cap 7. When it contacts water, the copper sulfate turns green-blue, thus causing the test strip 13 to change color intensively and in a manner that is visually easy to identify. When the test strip 13 is arranged on the outside of the end cap 7, it can therefore be immediately and easily determined with the filtering element 1 being removed whether the fluid to be filtered is contaminated with water. The test strip 13 does not have to be attached at the location shown in FIG. 1; instead, it can just as well be attached at another location, preferably one that is easily visible from the outside, for example on the top side of the end cap 7.

Figure 2:
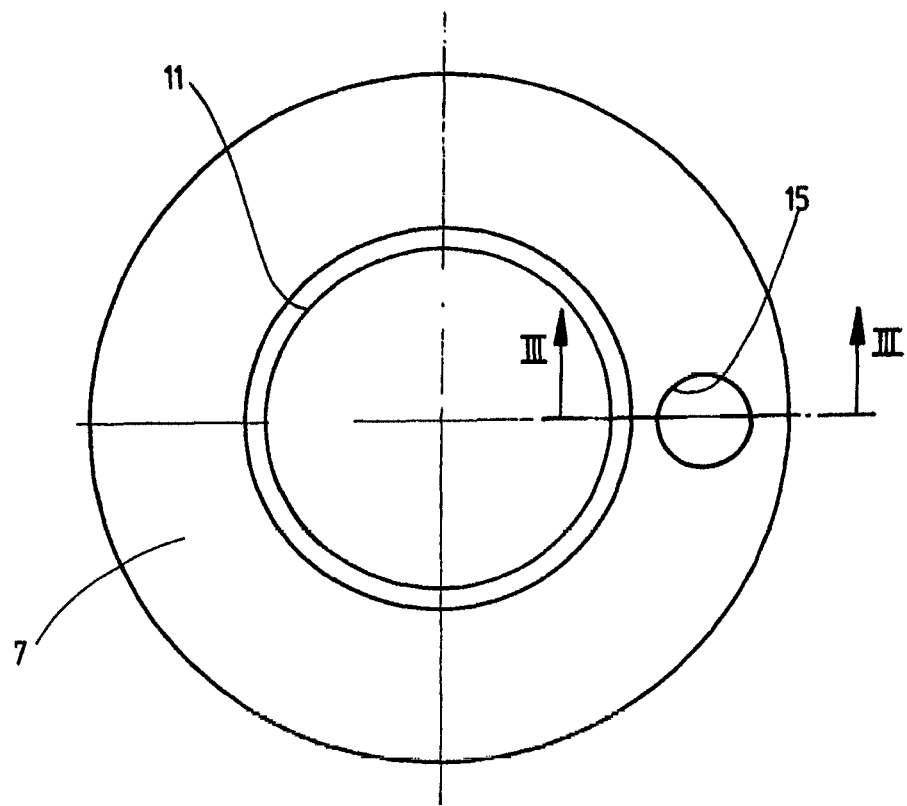
FIG. 2 shows a highly schematically simplified drawing of a plan view of a second exemplary embodiment of the filtering element according to the invention.
Figure 3:
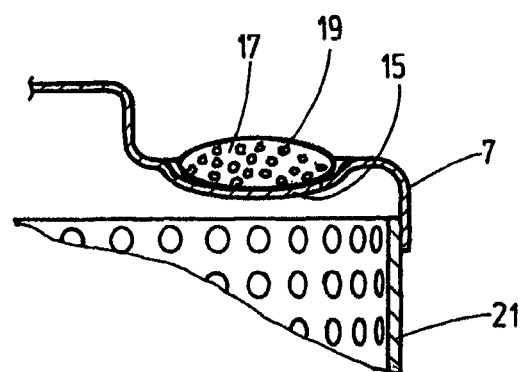
FIG. 3 shows a schematically simplified drawing of a partial longitudinal section following intersecting line III-III from FIG. 2.

FIGS. 2 and 3 illustrate a second exemplary embodiment in which a silica gel is used as the water indicator instead of a test strip 13. Silica gel is based on siliceous earth which is strongly hygroscopic. It is often used as a so-called blue gel when employed as a water indicator with added cobalt(II) chloride, wherein it changes color from blue to blue-pink to white upon contacting water. Alternatively, siliceous earth with added cobalt-free substances can be used as a so-called orange gel that changes color from orange to white upon absorbing water.

As shown in FIGS. 2 and 3, a concavity 15 is provided in the top side of the top end cap 7 as a receptacle for a test element 17 (FIG. 3) containing silica gel. As shown in FIG. 3, the silica gel is in the form of a granulate 19 within a permeable envelope made of paper or plastic glued into the concavity 15.

Figure 4:
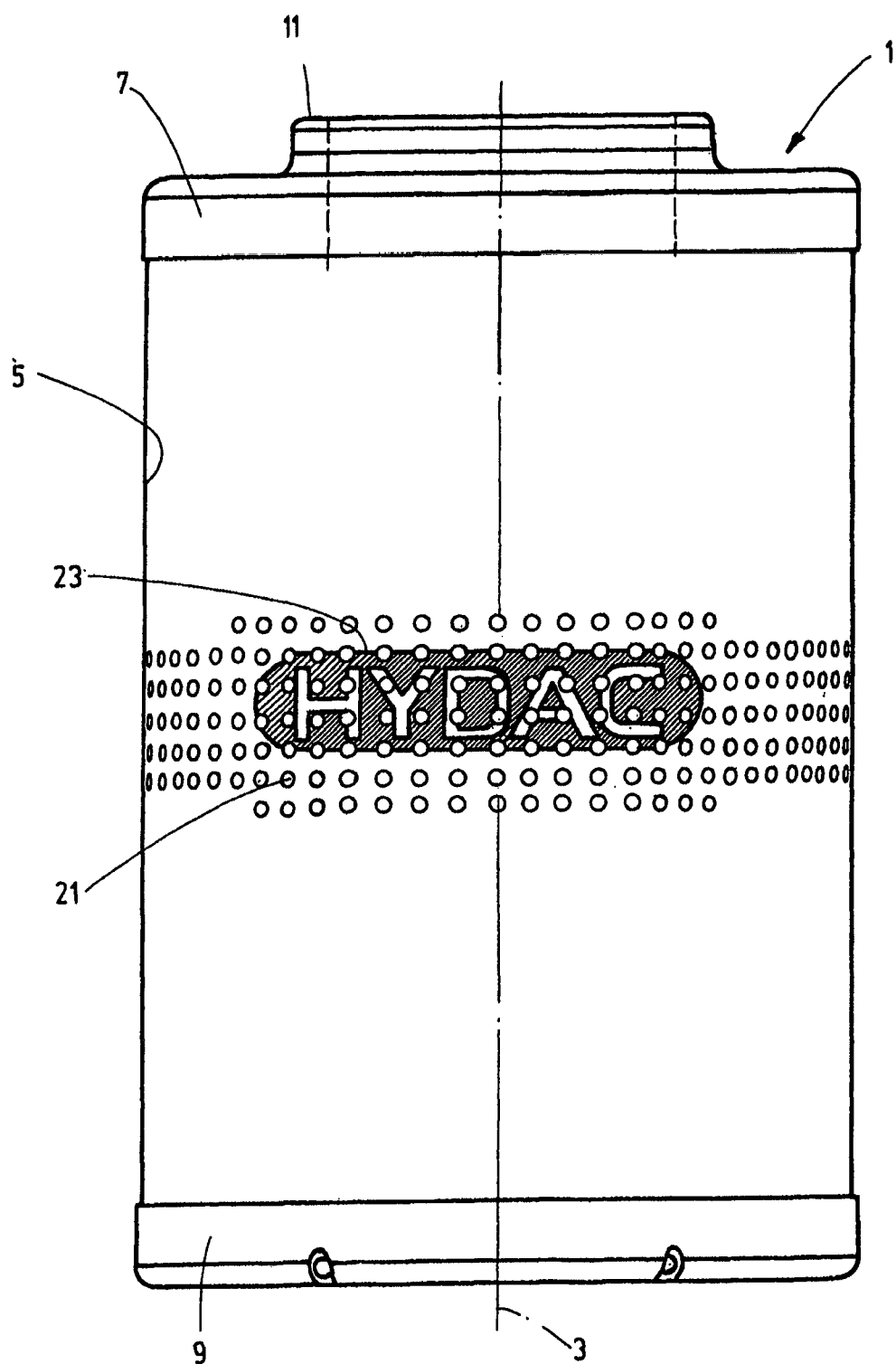
FIG. 4 shows a schematically simplified drawing of a side view of a filtering element according to a third exemplary embodiment of the invention.

FIG. 4 shows another exemplary embodiment in which a fluid-permeable supporting structure 21 forming the outer encasement of the filtering material 5 is provided with a printed marking 23 that forms legible lettering. In this example, the printed marking 23 forms the water indicator. When a supporting structure 21 is formed from a suitable plastic material, PET, a suitable printing ink can be used for printing to which a water indicator such as copper sulfate can be added so that the change in color which signals the presence of water occurs at corresponding areas of the marking 23 and is observable.

Instead of using copper sulfate or silica gel, other substances can be used such as indicators which are now being used in electronic devices like cell phones or the like that are sensitive to humidity and that turn red upon contacting water. Such indicators can be fastened by adhesion, for example to an end cap 7, 9 corresponding to the exemplary embodiment shown in FIG. 1.

What is claimed is:

1. A filtering element for filtering devices comprising:
   a cylindrical filtering material for the filtration of fluids defining an internal filtering cavity within the filtering material;
   a top and a bottom end cap as terminal encasements of said filtering material; and
   at least one water indicator which displays the presence of water in the fluid in a visually recognizable manner, wherein
   said at least one water indicator is provided on an outside of the filtering element and on an outside of one of said top and bottom end caps at a location coming into contact with fluid during filtration mode.

2. The filtering element according to claim 1, wherein said filtering element forms a removable filtering cartridge.

3. The filtering element according to claim 1, wherein the at least one water indicator is attached to one of said top and bottom end cap and is in the form of a test strip comprising copper sulfate.

4. The filtering element according to claim 1, wherein the filtering space defined by the filtering material is formed as a filtering cavity and/or is cylindrical.

5. The filtering element according to claim 1, wherein at least one of said end caps forms a circular encasement.

6. The filtering element according to claim 1, wherein the at least one water indicator signals the presence of water by changing color.

7. The filtering element according to claim 6, wherein the at least one water indicator irreversibly changes color in the presence of water.

8. The filtering element according to claim 1, wherein at least a substantial portion of said filtering space is provided with said filtering material.

9. The filtering element according to claim 1, wherein said top and bottom end caps are arranged on opposite sides of said filtering space along a longitudinal axis of said filtering element.

10. The filtering element according to claim 1, wherein a fluid-permeable supporting structure is provided, that forms an outer encasement of said filtering material.

11. The filtering element according to claim 10, wherein said fluid-permeable supporting structure is arranged coaxially with said filtering material along a longitudinal axis of said filtering element.

12. The filtering element according to claim 10, wherein said fluid-permeable supporting structure extends along a longitudinal axis of said filtering element from said top end cap to said bottom end cap.

13. The filtering element according to claim 1, wherein the at least one water indicator is arranged so that the water indicator is visually observable, at least when the filtering element is removed from the filtering device.

14. A filtering element for filtering devices comprising:
a cylindrical filtering material for the filtration of fluids defining an internal filtering cavity within the filtering material;
a top and a bottom end cap as terminal encasements of said filtering material; and
at least one water indicator which displays the presence of water in the fluid in a visually recognizable manner, wherein
said at least one water indicator is provided on an outside of the filtering element and on one of said top and bottom end caps at a location coming into contact with fluid during filtration mode; and
said at least one water indicator is in the form of a test strip.

\* \* \* \* \*